United States Patent
Kitamura et al.

(12)
(10) Patent No.: US 6,258,949 B1
(45) Date of Patent: Jul. 10, 2001

(54) APPARATUS AND PROCESS FOR PRODUCING ε-CAPROLACTAM

(75) Inventors: Masaru Kitamura; Yasumoto Shimazu, both of Niihama (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/526,885

(22) Filed: Mar. 16, 2000

(30) Foreign Application Priority Data

Mar. 16, 1999 (JP) .................................................. 11-069999

(51) Int. Cl.[7] .................................................. C07D 201/04
(52) U.S. Cl. ............................................................... 540/536
(58) Field of Search .............................................. 540/536

(56) References Cited

U.S. PATENT DOCUMENTS

| 2,373,358 | 4/1945 | Upham et al. ........................ 196/52 |
| 3,821,202 | 6/1974 | Schwarz et al. ............... 260/239.3 A |
| 4,017,482 | 4/1977 | Gath et al. ..................... 260/239.3 A |
| 4,141,896 | * 2/1979 | Immel et al. .................. 260/239.3 A |
| 4,248,728 | 2/1981 | Fuchs et al. .......................... 252/103 |
| 4,268,440 | * 5/1981 | Werther et al. ............... 260/239.3 A |

FOREIGN PATENT DOCUMENTS

| 0544530 | 6/1993 | (EP) . |
| 685181 | 12/1952 | (GB) . |

* cited by examiner

*Primary Examiner*—Bruck Kifle
(74) *Attorney, Agent, or Firm*—Birch, Stewart, Kolasch & Birch, LLP

(57) ABSTRACT

An apparatus for the production of ε-caprolactam is provided which comprises (i) a fluidized bed reactor having a solid catalyst therein for subjecting cyclohexanone oxime to a rearrangement reaction to obtain a reaction product containing unreacted cyclohexanone oxime and (ii) a fixed bed reactor packed with a solid catalyst for subjecting the unreacted cyclohexanone oxime to a rearrangement reaction to obtain ε-caprolactam. Using the apparatus, ε-caprolactam is obtained with a high yield.

4 Claims, 2 Drawing Sheets

APPARATUS AND PROCESS FOR PRODUCING ε-CAPROLACTAM

BACKGROUND OF THE INVENTION

1. Field of the Invention

The present invention relates to an apparatus for the production of ε-caprolactam and a process for producing ε-caprolactam using the apparatus. More precisely, the present invention relates to an apparatus for the production of ε-caprolactam which is capable of decreasing an amount of unreacted cyclohexanone oxime as an impurity, remaining in the reaction product ε-caprolactam and capable of increasing the yield of ε-caprolactam, and a process for producing ε-caprolactam using such an apparatus.

2. Description of Related Art

ε-Caprolactam is a key chemical product used as a raw material for Nylon or the like. For the production of ε-caprolactam, a process has been adopted in which cyclohexanone oxime is subjected to a Beckmann rearrangement reaction using fuming sulfuric acid under liquid phase conditions (liquid phase Beckmann rearrangement process). In addition to that, many variations for the production have been proposed in which cyclohexanone oxime is subjected to a Beckmann rearrangement reaction using a solid catalyst under gaseous phase conditions (gaseous phase Beckmann rearrangement process) [Examples of the catalyst include a boric acid catalyst (JP-A-53-37686, ibid. 46-12125), a silica-alumina catalyst (British Patent No. 881,927), a solid phosphoric acid catalyst (British Patent No. 881,956), a Y-type zeolite catalyst (Journal of Catalysis, 6,247 (1966)), a crystalline aluminosilicate catalyst (JP-A-57-139062) and the like.]

The conventional liquid phase Beckmann rearrangement process using fuming sulfuric acid, which is widely adopted in the industry, had not only problems such that a much amount of sulfuric acid is required but also problems such that a large amount of ammonium sulfate, for example, as much as about 1.7 ton of ammonium sulfate per ton of ε-caprolactam is produced as the by-product since neutralization of the sulfuric acid with ammonia is necessary for recovering ε-caprolactam from the reaction product of the Beckmann rearrangement reaction.

On the other hand, the gaseous phase Beckmann rearrangement process using a solid catalyst has advantages such that no ammonium sulfate is produced. However, the gaseous phase Beckmann rearrangement process has a problem such that carbonaceous substances deposit on the solid catalyst during the reaction in the process, resulting in coverage of active sites with the carbonaceous substances, which leads to gradual deactivation of the catalyst. In order to regenerate the deteriorated catalytic activity, a method is proposed in which the carbonaceous substances on the catalyst is oxidized and removed by an oxygen-containing gas. However, this method causes other problems in a fixed bed reaction system such that the production of ε-caprolactam is interrupted during the regeneration operation for the catalyst, and a switching operation between the production of ε-caprolactam and the regeneration of the catalyst is troublesome. Another method for the regeneration is also known in which both the gaseous phase Beckmann rearrangement reaction (i.e., the production of ε-caprolactam) and the regeneration of the catalyst are respectively performed in each fluidized bed system and the operations of the reaction and the regeneration are continuously carried out at the same time by circulating the catalyst through the reactor and the regenerator (for example, JP-A-55-53267).

Although the above described problems have been solved by such a method of fluidized bed system, there are many problems furthermore in the conventional gaseous phase Beckmann rearrangement reaction such that all of cyclohexanone oxime can not be consumed in the reaction. It is unavoidable that some unreacted cyclohexanone oxime remains in the reaction product. However, it is not easy to perform separation of cyclohexanone oxime from ε-caprolactam by a commonly used distillation procedure. Since, however, a high-purified ε-caprolactam is needed for producing Nylon or the like, separation byaprocedure such as crystallization, extraction, azeotropic distillation or the like is necessary, while such a procedure is costly and undesirably from the industrial viewpoint. Under such a circumstance, a new process has been desired which decreses the amount of unreacted cyclohexanone oxime as possible in the reaction product in the step of gaseous phase Beckmann rearrangement reaction.

In JP-A-46-3727, it is pointed out that separation of cyclohexanone oxime from ε-caprolactam by a physical separation method is quite impossible, or too costly if possible, since both compounds have similar physical properties. In order to avoid this problem, a process is disclosed in which a cyclohexanone oxime-containing ε-caprolactam obtained by the gaseous phase Beckmann rearrangement reaction is treated with sulfur dioxide at a temperature of from 70 to 170° C. In this process, however, a gaseous crude ε-caprolactam which is formed at an elevated temperature of 300° C. or higher should be cooled to 170° C. or lower to be liquefied before reacting with gaseous sulfur dioxide and, therefore, the procedures thereof are troublesome. In addition, a step for removing sulfur dioxide is also needed.

In JP-A-51-52188, a process is disclosed in which a crude ε-caprolactam obtained by the gaseous phase Beckmann rearrangement reaction is mixed with an acidic mixture obtained by Beckmann rearrangement of cyclohexanone oxime using fuming sulfuric acid. Although nothing is described in the specification about cyclohexanone oxime remaining in the crude ε-caprolactam obtained by the gaseous phase Beckmann rearrangement reaction, the cyclohexanone oxime contained as an impurity may be converted to ε-caprolactam by Beckmann rearrangement with the treatment in a strongly acidic medium. This process, however, is not preferred because ammonium sulfate is produced due to the use of fuming sulfuric acid.

SUMMARY AND OBJECT OF THE INVENTION

The present invention is attained under these circumstances. The present inventors have made extensive studies searching for a process for producing ε-caprolactam by the gaseous phase Beckmann rearrangement reaction of cyclohexanone oxime in which the amount of cyclohexanone oxime remaining in the reaction product is small and the yield of ε-caprolactam is improved. As a result, it has been found that ε-caprolactam having little amount of cyclohexanone oxime is obtained as a reaction product with a high yield of ε-caprolactam when a gaseous phase Beckmann rearrangement reaction is carried out in the presence of a solid catalyst in a fluidized bed reactor to obtain a reaction product containing unreacted cyclohexanone oxime and then the unreacted cyclohexanone oxime contained in the reaction product is subjected to a gaseous phase Beckmann rearrangement reaction in the presence of a solid catalyst in a fixed bed reactor. The present invention has been accomplished on the basis of the above findings.

Thus, the present invention first provides an apparatus for the production of ε-caprolactam with a gaseous phase Beckmann rearrangement reaction of cyclohexanone oxime using a solid catalyst, which comprises (i) a fluidized bed reactor having a solid catalyst therein for subjecting cyclohexanone oxime to a gaseous phase Beckmann rearrangement reaction to obtain a first reaction product containing unreacted cyclohexanone oxime and (ii) a fixed bed reactor packed with a solid catalyst, which is placed in a downstream of the fluidized bed reactor, for subjecting the unreacted cyclohexanone oxime contained in the first reaction product to a gaseous phase Beckmann rearrangement reaction to obtain a second reaction product mainly containing ε-caprolactam.

Secondly, the present invention provides a process for producing ε-caprolactam which comprises the steps of (i) subjecting cyclohexanone oxime to a gaseous phase Beckmann rearrangement reaction using a solid catalyst in a fluidized bed reacor to obtain a first reaction product containing unreacted cyclohexanone oxime, and then (ii) subjecting the unreacted cyclohexanone oxime contained in the first reaction product to a gaseous phase Beckmann rearrangement reaction using a solid catalyst in a fixed bed reactor to obtain a second reaction product mainly containing ε-caprolactam.

DETAILED DESCRIPTION OF THE INVENTION

Figure 1:
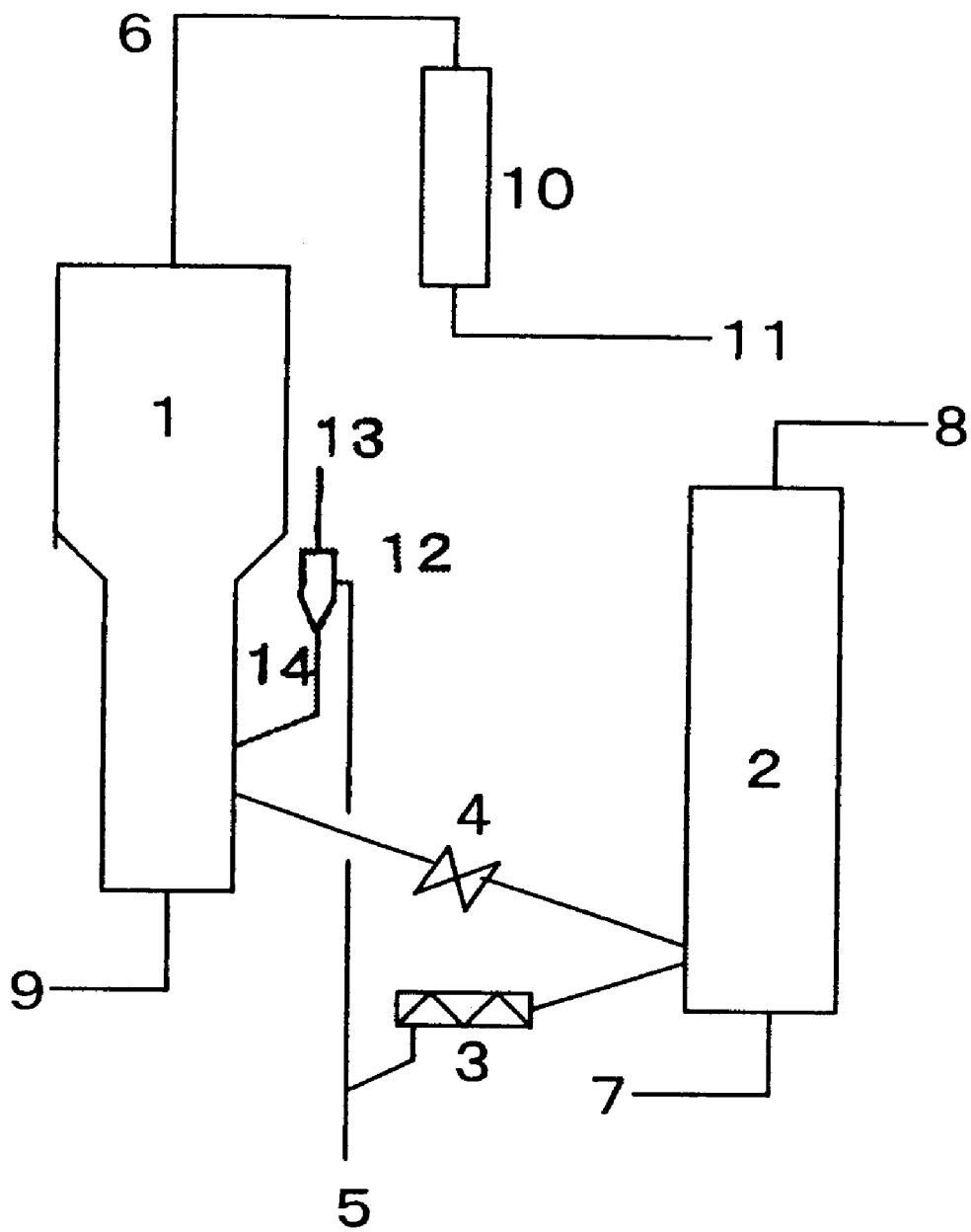
FIG. 1 is a schematic view of an apparatus for producing ε-caprolactam from cyclohexanone oxime by a Beckmann rearrangement reaction in the present invention.

In producing ε-caprolactam in the present invention, an apparatus is utilized which comprises a fluidized bed reactor and a fixed bed reactor. Specifically, the apparatus comprises (i) a fluidized bed reactor having a solid catalyst therein for subjecting cyclohexanone oxime to a gaseous phase Beckmann rearrangement reaction to obtain a first reaction product containing unreacted cyclohexanone oxime and (ii) a fixed bed reactor packed with a solid catalyst, which is placed in a downstream of the fluidized bed reactor, for subjecting the unreacted cyclohexanone oxime contained in the first reaction product to a gaseous phase Beckmann rearrangement reaction to obtain a second reaction product mainly containing ε-caprolactam.

For carrying out the present invention, using such a apparatus, cyclohexanone oxime is first subjected to a gaseous phase Beckmann rearrangement reaction in a fluidized bed reactor having a solid catalyst therein to obtain a gaseous reaction product containing unreacted cyclohexanone oxime. Then, the reaction product containing unreacted cyclohexanone oxime is withdrawn from the fluidized bed reactor and introduced into a fixed bed reactor packed with a solid catalyst to conduct a gaseous Beckmann rearrangement reaction of the unreacted cyclohexanone oxime to obtain a reaction product mainly containing ε-caprolactam. According to the present invention, ε-caprolactam having a small amount of cyclohexanone oxime is produced as a reaction product with a high yield of ε-caprolactam.

In carrying out the present invention, the rearrangement reaction of cyclohexanone oxime to ε-caprolactam may be conducted in a known manner. Cyclohexanone oxime may be used either in a vapor form or in a liquid form, and is usually used in the vapor (gaseous) form. Cyclohexanone oxime is introduced into the fluidized bed reactor in which a solid catalyst is kept at the reaction temperature. The rearrangement reaction may be carried out at a reaction temperature of from about 250° C. to about 450° C., preferably from about 300° C. to about 400° C. A reaction pressure is not particularly limited and may fall within a range of from about 10 kPa to about 0.5 MPa, preferably from about 50 kPa to about 0.3 MPa.

A space velocity (WHSV) of cyclohexanone oxime, i.e., a feeding rate of cyclohexanone oxime (kg/hour) per weight (kg) of catalyst, in the fluidized bed reactor may fall within a range of from about $0.1\ h^{-1}$ to about $20\ h^{-1}$, preferably within a range of from about $0.2\ h^{-1}$ to about $10^{-1}$.

In carrying out the Beckmann rearrangement reaction of cyclohexanone oxime, a lower alcohol having carbon atoms of 1 to 6 may be used together with cyclohexanone oxime. Examples of the lower alcohol include methanol, ethanol, n-propanol, isopropanol, n-butanol, sec-butanol, isobutanol, n-amyl alcohol, n-hexanol and the like. The lower alcohol is used independently orin combination thereof. Among them, a use of methanol or ethanol is preferred.

When the lower alcohol is used, an amount of the lower alcohol to used may fall within a range of from about 0.1 time to about 20 times, preferably within a range of from about 0.2 time to about 10 times, by weight base on cyclohexanone oxime. The use of the lower alcohol exhibits favorable effects on selectivity to ε-caprolactam and a catalyst life.

It is also advantageous to use water when cyclohexanone oxime is introduced into the reactor. The amount of water may be 2.5 times the mole amount of cyclohexanone oxime or less.

The solid catalyst applied in the fluidized bed reactor may be any solid catalyst known in this field. A crystalline zeolite, especially a pentasil-type zeolite, is preferred. Among the pentasil-type zeolite, particularly preferred is MFI zeolite. The crystalline zeolites has a skeleton of zeolite which is composed of silicon as a main component and another component (Me). Examples of the crystalline zeolite include crystalline aluminosolicates and crystalline metallosilicates. Examples of the crystalline metallosilicates include those having an atomic ratio Si/Me of usually 5 or more, preferably 500 or more, wherein Me is at least one atom selected from B, Al, Ga, Fe, Ti and Zr. The atomic ratio Si/Me can be measured by atomic absorption spectrophotometry, fluorescent X-ray analysis or other methods.

The crystalline zeolite used in the fluidized bed can be prepared by a known process. Examples of the process include a method in which a silica source, water, quaternary ammonium and, if necessary, a metal source are mixed and subjected to a hydrothermal reaction in an autoclave to form crystals, followed by being dried, calcined, ion-exchanged with an ammonium salt or the like and dried.

A shape of the solid catalyst used in the fluidized bed reactor is not particularly limited and may be particles having an average diameter of from 20 μm to 0.3 mm.

In the present invention, the reaction product containing unreacted cyclohexanone oxime is withdrawn from the fluidized bed reactor and then introduced into a fixed bed reactor so that the unreacted cyclohexanone oxime reacts further.

A shape of the fixed bed reactor is not particularly limited and a fixed bed commonly known in this field may be utilized.

A reaction temperature and a reaction pressure in the fixed bed reactor may be within the same ranges as those for the fluidized bed reactor which are described above.

A solid catalyst applied in the fixed bed reactor may be a zeolite catalyst similar to that for the fluidized bed reactor. A pentasil-type zeolite catalyst is preferably used. It is desirable that the solid catalyst for the fixed bed reactor has a high mechanical strength, a large pore volume and a low pressure drop. As such a solid catalyst, various kinds of shapes such as sphere, pellet, prism, macaroni, profile pellet and profile pellet with profile hollow (for example, honeycomb) and sizes such as an average particle size of from 0.5 mm to 10 mm can be applied. When a molded catalyst is used, any known processes such as extruding, pressing and dish rolling can be adopted as a molding process for producing the molded catalyst.

In the present invention, the gaseous reaction product mainly containing ε-caprolactam, which is withdrawn from the fixed bed reactor obtained after the reaction therein, may be subjected to a separation procedure of ε-caprolactam from reaction product in a known method. For example, the gaseous reaction product is cooled to be condensed and then purified by a procedure such as extraction, distillation or crystallization to obtain a purified ε-caprolactam.

The present invention is described below in more detail referring to appended drawings.

FIG. 1 is a schematic view of an apparatus of the present invention, for the production of ε-caprolactam by subjecting cyclohexanone oxime to a gaseous phase Beckmann rearrangement reaction in the presence of a solid catalyst, which comprises a fluidized bed reactor and a fixed bed reactor.

In FIG. 1, 1 denotes a fluidized bed reactor, 2 a regenerator for catalyst in a fluidized bed system, 3 a screw feeder, 4 a control valve, 5, 6, 7, 8, 9, 11, 13 and 14 a pipe, 10 a fixed bed reactor and 12 a cyclone.

In carrying out the present invention using an apparatus illustrated in FIG. 1, cyclohexanone oxime is mixed with an alcohol such as methanol, and then vaporized, and introduced into a fluidized bed reactor 1 in a gaseous form (referred to as a raw material gas) through a pipe 9. It is preferred that an inert gas such as nitrogen or argon is introduced into the reactor 1 together with the raw material gas through the pipe 9. In the reactor 1, particles of solid catalyst having a diameter of 0.3 mm or less are placed and fluidized by the raw material gas and the inert gas which are introduced through the pipe 9, and cyclohexanone oxime in the raw material gas is subjected to a Beckmann rearrangement reaction therein to provide a reaction product.

The space velocity (WHSV) of cyclohexanone oxime, i.e., a feeding rate of cyclohexanone oxime (kg/hour) per weight (kg) of catalyst, falls within a range of from about 0.1 $h^{-1}$ to about 20 $h^{-1}$, preferably from about 0.2 $h^{-1}$ to about 10 $h^{-1}$. The reaction temperature falls within a range of from 250° C. to 450° C., preferably from 300° C. to 400° C. The reaction pressure falls within a range of from 10 kPa to 0.5 MPa, preferably from 50 kPa to 0.3 MPa.

Depending on the reaction conditions for the Beckmann rearrangement reaction in the reactor 1, the obtained reaction product may contain unreacted cyclohexanone oxime. In the present invention, the reaction product obtained in the reactor 1 (in the gaseous form) is withdrawn through a pipe 6 and introduced into a reactor 10 in which the unreacted cyclohexanone oxime in the reaction product is subjected to a Beckmann rearrangement reaction to be converted into ε-caprolactam.

The reactor 10 is a fixed bed reactor. In the reactor 10 are packed moldings of solid catalyst having a shape of tablet, prism, honeycomb or the like and a size of from 0.5 mm to 10 mm. The reaction conditions in the reactor 10 are almost the same as those in the reactor 1 except that a space velocity (WHSV) of the reaction product, i.e., a feeding rate of the reaction product (which contains ε-caprolactam, the unreacted cyclohexanone oxime and by-product impurities) (kg/hour) per weight (kg) of catalyst in the fixed bed, falls within a range of from about 1 $h^{-1}$ to about 50 $h^{-1}$, preferably from about 2 $^{-1}$ to about 40 $h^{-1}$. The reaction temperature falls within a range of from 300° C. to 450° C., preferably from 330° C. to 400° C. The reaction pressure falls within a range of from 10 kPa to 0.5 MPa, preferably from 50 kPa to 0.3 MPa.

The resulting reaction product (in a gaseous form) obtained after the completion of the reaction in the reactor 10 may be continuously withdrawn through a pipe 11 and may be treated with a commonly used procedure in order to obtain a purified ε-caprolactam therefrom. For example, the reaction product is cooled to be condensed and then subjected to a known purification procedure such as extraction, distillation or crystallization to obtain ε-caprolactam having a desired purity.

As well known, a Beckmann rearrangement reaction is an exothermic reaction. Therefore, the reactor 1 in the fluidized bed system preferably has a cooler (not shown) for cooling equipped therein so that the catalysts are not exposed to excessively high temperature. On the other hand, as the fixed bed reactor 10, a so-called adiabatic reactor having no cooler can be utilized, since the amount of cyclohexanone oxime to be reacted in the reactor 10 is small so that the heat release is little. This allows lowering in equipment cost for the reactor 10. When such an adiabatic reactor having no cooler is adopted for the fixed bed reactor 10, the amount of cyclohexanone oxime to be introduced into the reactor 10 should be controlled so that an excessive introduction of cyclohexanone oxime is avoided in order to keep the heat load onto the reactor 10 below a certain level. Therefore, it is desirable to adopt reaction conditions in the fluidized bed reactor 1 which allow a conversion of cyclohexanone oxime therein to be 90% or more, preferably 95% or more. It is also possible to equip a cooling apparatus in the fixed bed reactor 10 to control the reaction temperature in the reactor 10. When such an apparatus is equipped in the reactor 10, no limitation may be particularly needed onto the conditions (which effect on conversion of cyclohexanone oxime) adopted in the reactor 1.

In a process for producing ε-caprolactam by subjecting cyclohexanone oxime to a gaseous phase Beckmann rearrangement reaction using a solid catalyst, the solid catalyst gradually loses its activity due to deposition of carbonaceous substances on the surface of the solid catalyst while the solid catalyst has been used for a long period of time. Therefore, the catalyst should be reused after being regenerated by treating with an oxygen-containing gas so as to burn and remove the carbonaceous substances. The regeneration treatment of a solid catalyst used in a fluidized bed reactor is preferably carried out in a regenerator in the fluidized bed system. In FIG. 1, 2 denotes a regenerator for the catalyst in a fluidized bed system and 4 denotes a control valve with a pipe feeding the solid catalyst having a lowered activity from the reactor 1 to the regenerator 2. The solid catalyst in a suitable amount is continuously or intermittently fed from the reactor 1 to the regenerator 2 by adjusting an opening of the valve 4. In order to regenerate the solid catalyst by burning the carbonaceous substances deposited on the surface of the solid catalyst, an oxygen-containing gas such as air is introduced into the regenerator 2 through a piping 7. As the oxygen-containing gas, air is preferably used as it is, while the air having an oxygen concentration of 20% or less may also be used which is obtained after mixing with an inert gas such as nitrogen. The temperature for the regeneration treatment falls within a range of 350° C. to 700° C., preferably from 400° C. to 600° C. When the temperature is lower than 350° C., the burning of carbonaceous substances deposited on the catalyst tends to be insufficient and the remaining amount of nitrogen component in the catalyst, which is also a substance lowering the activity of the catalyst, tends to be too large and, therefore, the activity of the catalyst may not be sufficiently recovered. When the temperature is higher than 700° C., the solid catalyst such as zeolite may decompose and the activity and selectivity of the catalyst tends to be gradually lowered. The pressure for the regeneration treatment falls within approximately the same range as that for the Beckmann rearrangement reaction. The residence time of the catalyst in the regenerator 2 is from 0.5 hour to 500 hours in average.

A waste gas produced by the burning in the regeneration treatment is discharged through a pipe 8. The solid catalyst obtained after the regeneration treatment is withdrawn from the regenerator 2 via a screw feeder 3 which can continuously and quantitatively discharge the solid catalyst. Nitrogen gas is introduced from a pipe 5 to a cyclone 12. The solid catalyst is separated from the nitrogen gas in the cyclone 12, introduced through a pipe 14 into the reactor 1 and reused in the reactor 1. The remaining nitrogen gas is discharged through a pipe 13.

FIG. 1 shows one embodiment of the present invention in which the reaction product obtained from the fluidized bed reactor 1 is introduced into the fixed bed reactor 10 connected in series to the reactor 1. In this case, when the activity of the solid catalyst in the reactor 10 is lowered and the regeneration treatment of the catalyst is required, the Beckmann rearrangement reaction in the reactor 1 should be unwillingly interrupted while the solid catalyst is regenerated in the reactor 10. Therefore, it is preferred that more than one fixed bed reactors, preferably two or more fixed bed reactors, are provided per one fluidized bed reactor 1 for the rearrangement reaction.

Figure 2:
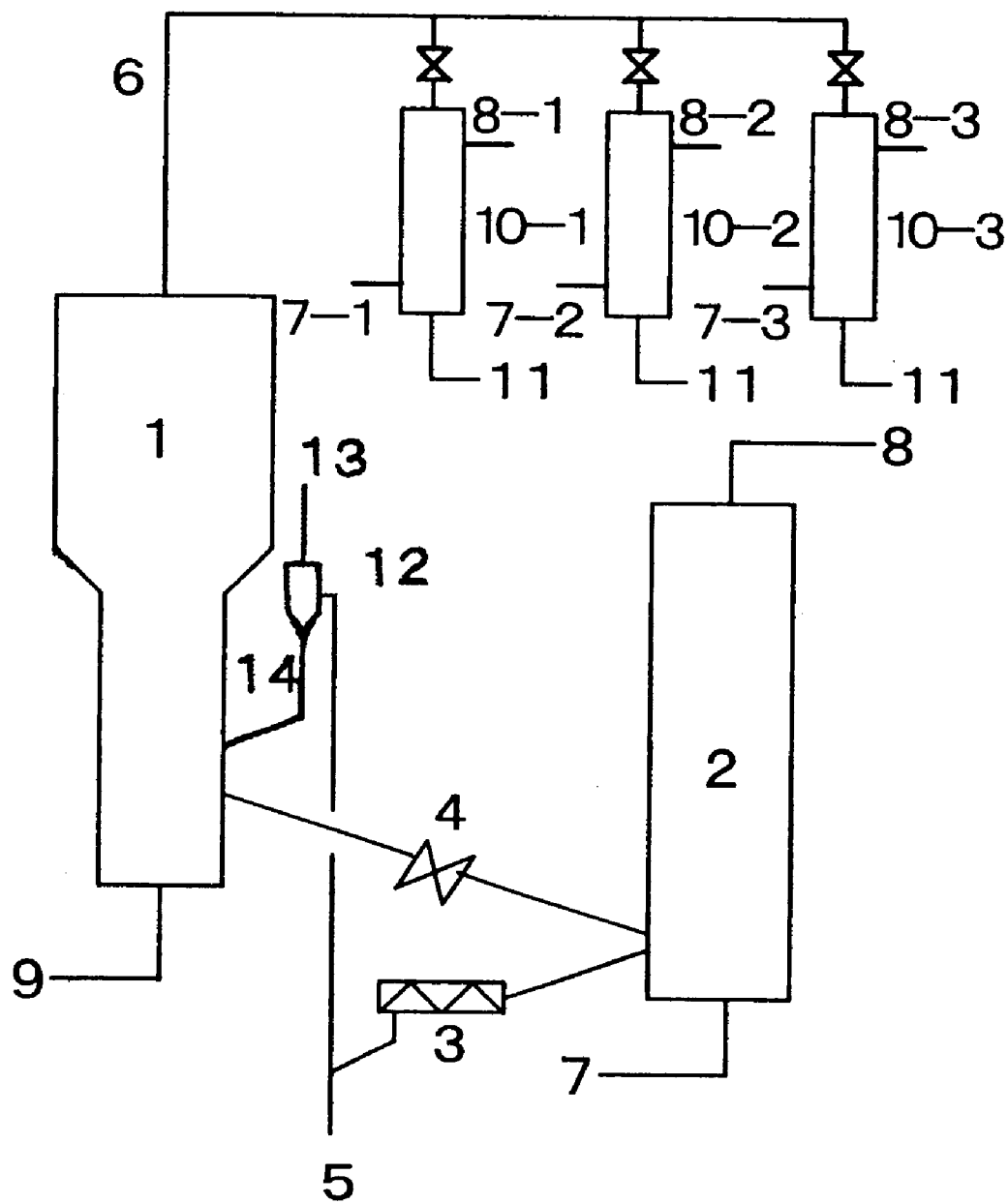
FIG. 2 is a schematic view of another apparatus for producing ε-caprolactam from cyclohexanone oxime by a Beckmann rearrangement reaction in the present invention.

FIG. 2 shows another embodiment of the present invention of such a system. In this system, a plurality of fixed bed reactors such as three fixed bed reactors 10-1, 10-2 and 10-3 are connected in parallel to a fluidized bed reactor 1 in the downstream of the fluidized bed reactor 1. Respective fixed bed reactors can be blocked by sluice valves away from the introduction of the gaseous reaction product, which is withdrawn from the fluidized bed reactor 1 and may be introduced to each fixed bed reactor through a pipe 6.

When only two fixed bed reactors (for example, the reactors 10-1 and 10-2) are placed, the sluice valve for the reactor 10-2 is closed and an oxygen-containing gas is introduced into the reactor 10-2 through a pipe 7-2 so that the catalyst in the reactor 10-2 is subjected to the regeneration treatment, while the gaseous reaction product is introduced into the reactor 10-1 through the pipe 6. After the regeneration treatment in the reactor 10-2, an inert gas such as nitrogen gas is passed through the pipe 7-2 to replace the interior of the reactor 10-2 with the inert gas. When the activity of the catalyst packed in the reactor 10-1 is lowered with the passage of time, the introduction of reaction product produced in the reactor 1 is switched by the sluice valves from the reactor 10-1 to the reactor 10-2, and an oxygen-containing gas is introduced into the reactor 10-1 through a pipe 7-1 so that the catalyst in the reactor 10-1 is subjected to the regeneration treatment. In this manner, the reaction product obtained in the fluidized bed reactor 1 is continuously subjected to the Beckmann rearrangement reaction in one of two fixed bed reactors 10-1 and 10-2 by interchangeably using one of the fixed bed reactors. When three or more fixed bed reactors are used, the fixed reactor where the rearrangement reaction is conducted by the introduction of the reaction product obtained in the fluidized bed 1 reactor is changed in turn by switching the sluice valves in the same manner as described above.

The conditions, i.e. temperature, pressure, oxygen concentration and so on, for the regeneration treatment of the catalyst in the fixed bed reactors may be similar to those for the regeneration treatment of the catalyst in the fluidized bed reactor as described above. The period of time required for the regeneration treatment depends on temperature, oxygen concentration and pressure and may be suitably from 10 hours to 30 days.

When a plurality of fluidized bed reactors, for example two fluidized bed reactors, are utilized for the Beckmann rearrangement reaction of cyclohexanone oxime at the same time, it is not necessary to equip two fixed bed reactors for each fluidized bed reactor, i.e., four fixed bed reactors in total, as long as the regeneration treatment for catalyst in the 13 fixed bed reactors having a lowered activity can be conducted without interrupting the Beckmann rearrangement reaction of cyclohexanone oxime in the fluidized bed reactors. If this requirement is met, the use of three fixed bed reactors for regeneration treatment is acceptable even when two fluidized bed reactors is used at the same time.

As described above in detail, according to the present invention, $\epsilon$-caprolactam is obtained with a high yield using an apparatus comprising a fluidized bed reactor and a fixed bed reactor placed in a downstream of the fluidized bed reactor. Furthermore, according to the present invention, when an apparatus is adopted in which more than one fixed bed reactors are installed per one fluidized bed reactor as illustrated in FIG. 2 so that a Beckmann rearrangement reaction of unreacted cyclohexanone oxime (contained in the reaction product obtained in the fluidized bed reactor) and regeneration treatment of catalyst (having a lowered activity in the reaction) are conducted at the same time in respective fixed bed reactors, a long-term and steady production of $\epsilon$-caprolactam is carried out without a shutdown of the operations thereof, with a high yield of $\epsilon$-caprolactam, while keeping a high conversion of cyclohexanone oxime. Therefore, the present invention has great industrial advantages.

EXAMPLES

The present invention is described in more detail by following Examples, which should not be construed as a limitation upon the scope of the invention.

In Examples, the apparatus shown in FIG. 1 was used and conversion of cyclohexanone oxime was calculated by the following formula:

Conversion of cyclohexanone oxime (%)=[1−(molar amount of unreacted cyclohexanone oxime)/(molar amount of cyclohexanone oxime fed in the reaction)]×100

Example 1

A catalyst in a form of tablets (3 mm in diameter and 3 mm in length) was obtained by extruding a high-silica MFI zeolite consisting substantially of silicon oxide. Into a stainless steel tube having a diameter of 40 mm and a length of 400 mm was packed 75 g of the catalyst to prepare a fixed bed reactor 10. Into a straight stainless steel tube having a diameter of 80 mm and a length of 1,000 mm equipped with a freeboard part having a diameter of 200 mm and a length of 1,000 mm, was respectively placed 250 g of a catalyst in a form of fine powders having a diameter of 0.3 mm or less comprising MFI zeolite as a main component to prepare a fluidized bed reactor 1. Into a straight stainless steel tube having a diameter of 65 mm and a length of 2,000 mm was placed 400 g of a catalyst in a form of fine powders having a diameter of 0.3 mm or less comprising MFI zeolite as a main component to prepare a regenerator 2.

The fluidized bed reactor 1, the fixed bed reactor 10 and the regenerator 2 were connected one another as shown in FIG. 1. The particles of the catalyst in the fluidized bed reactor 1 were fluidized by introducing nitrogen gas through a pipe 9 at a rate of 0.4 m$^3$/hour. The temperature in the fluidized bed reactor 1 was elevated to 350° C. On the other hand, air was introduced through a pipe 7 into the regenerator 2 at a rate of 0.2 m$^3$/hour and the temperature in the regenerator 2 was elevated to 500° C., to fluidize the catalyst therein at the elevated temperature 500° C. After the temperatures in the fluidized bed reactor 1, the fixed bed reactor 10 and the regenerator 2 were stabilized, cyclohexanone oxime in a gaseous form as a raw material was fed through the pipe 9 into the fluidized bed reactor 1 at a rate of 1,260 g/hour together with gaseous methanol at a rate of 2,240 g/hour. In addition, nitrogen gas was introduced from a pipe 5 to the cyclone 12 at a rate of 1.0 m$^3$/hour.

By controlling an opening of valve 4 and a screw feeder 3, the catalyst was circulated from the fluidized bed reactor 1 to the regenerator 2 and from the regenerator 2 to the fluidized bed reactor 1 at a rate of 20 g/hour in terms of the weight of catalyst.

After the passage of 67 hours, the resulting reaction product was withdrawn through a pipe 11 to outside the system and analyzed. As a result, it was revealed that the reaction product contained cyclohexanone oxime at a concentration of 2,000 ppm based on ε-caprolactam therein.

Comparative Example 1

The same reactions and operations as in Example 1 were conducted except that the fixed bed reactor 10 was omitted. After the passage of 67 hours, it was revealed that the reaction product withdrawn through the pipe 11 contained cyclohexanone oxime at the concentration of 4,000 ppm based on ε-caprolactam therein.

Example 2

The same reactions and operations as in Example 1 were conducted except that the shape of catalyst packed in the fixed bed reactor 10 was changed to macaroni-type tablets having a diameter of 5 mm and a length of 5 mm with a pore having a diameter of 2 mm, and the amount of the catalyst packed in the fixed bed reactor 10 was changed to 80 g. After the passage of 97 hours, it was revealed that the reaction product withdrawn through the pipe 11 contained cyclohexanone oxime at the concentration of 1,000 ppm based on ε-caprolactam therein.

Comparative Example 2

The same reactions and operations as in Example 2 were conducted except that the fixed bed reactor 10 was omitted. After the passage of 97 hours, it was revealed that the reaction product withdrawn through the pipe 11 contained cyclohexanone oxime at the concentration of 4,000 ppm based on ε-caprolactam therein.

What is claimed is:

1. A process for producing ε-caprolactam which comprises the steps of (i) subjecting cyclohexanone oxime to a gaseous phase Beckmann rearrangement reaction using a solid catalyst in a fluidized bed reactor to obtain a first reaction product containing unreacted cyclohexanone oxime in an amount of 5% or less based on cyclohexanone oxime which is fed in step (i), and then (ii) subjecting said unreacted cyclohexanone oxime contained in the first reaction product to a gaseous phase Beckmann rearrangement reaction using a solid catalyst in a fixed bed reactor to obtain a second reaction product mainly containing ε-caprolactam.

2. The process according to claim 1, which further comprises the steps of (iii) withdrawing the solid catalyst from the fluidized bed reactor in step (i) to introduce the catalyst into another fluidized bed reactor, (iv) treating the catalyst with an oxygen-containing gas and (v) returning the treated catalyst to the fluidized bed reactor in step (i).

3. The process according to claim 1 or 2, wherein said solid catalyst is a pentasil-type zeolite.

4. The process according to claim 1 or 2, wherein said fixed bed reactor is of the thermal insulation type.

* * * * *